United States Patent [19]

McCausland

[11] Patent Number: 5,765,223
[45] Date of Patent: Jun. 16, 1998

[54] FACE SHIELD

[76] Inventor: Mary L. McCausland, 16629 Lescot Ter., Rockville, Md. 20853

[21] Appl. No.: 658,520

[22] Filed: Jun. 4, 1996

[51] Int. Cl.$^6$ .............................. A61F 9/00; A61F 9/02; A61F 9/06
[52] U.S. Cl. .............................. 2/9; 2/426; 2/427; 2/429; 2/435; 2/436
[58] Field of Search .............................. 2/9, 425, 427, 2/429, 430, 431, 432, 435, 436, 437, 438, 439; 128/201.24, 206.19, 206.15, 206.22, 207.12

[56] References Cited

U.S. PATENT DOCUMENTS

| | | | |
|---|---|---|---|
| 2,655,656 | 10/1953 | Moeller | 2/436 |
| 3,214,767 | 11/1965 | Weber | 2/9 |
| 4,621,378 | 11/1986 | Hatchman | 2/9 |
| 4,701,965 | 10/1987 | Landis | 2/9 |
| 4,852,185 | 8/1989 | Olson | 2/9 |
| 4,945,573 | 8/1990 | Landis | 2/9 |
| 4,964,171 | 10/1990 | Landis | 2/9 |
| 5,303,423 | 4/1994 | Gazzara et al. | |
| 5,440,760 | 8/1995 | Highsmith | 2/9 |

*Primary Examiner*—Jeanette E. Chapman
*Attorney, Agent, or Firm*—Myers, Liniak & Berenato

[57] ABSTRACT

A face shield is disclosed that includes a headband with an inner and outer surface, first and second ends and a visor between a portion of the inner and outer surfaces that tapers from a maximum width at the midpoint between the first and second ends to a minimum at a first point spaced a distance from the first end and at a second point spaced a distance from the second end, a flexible fluid impervious transparent cover removably attached to the outer edge of said headband, and means for adjustably securing the shield to a wearer's head. This face shield permits a wearer to comfortably wear eye glasses and/or breathing apparatus under the shield. Also, the flexible cover can be readily removed and replaced if damaged.

6 Claims, 4 Drawing Sheets

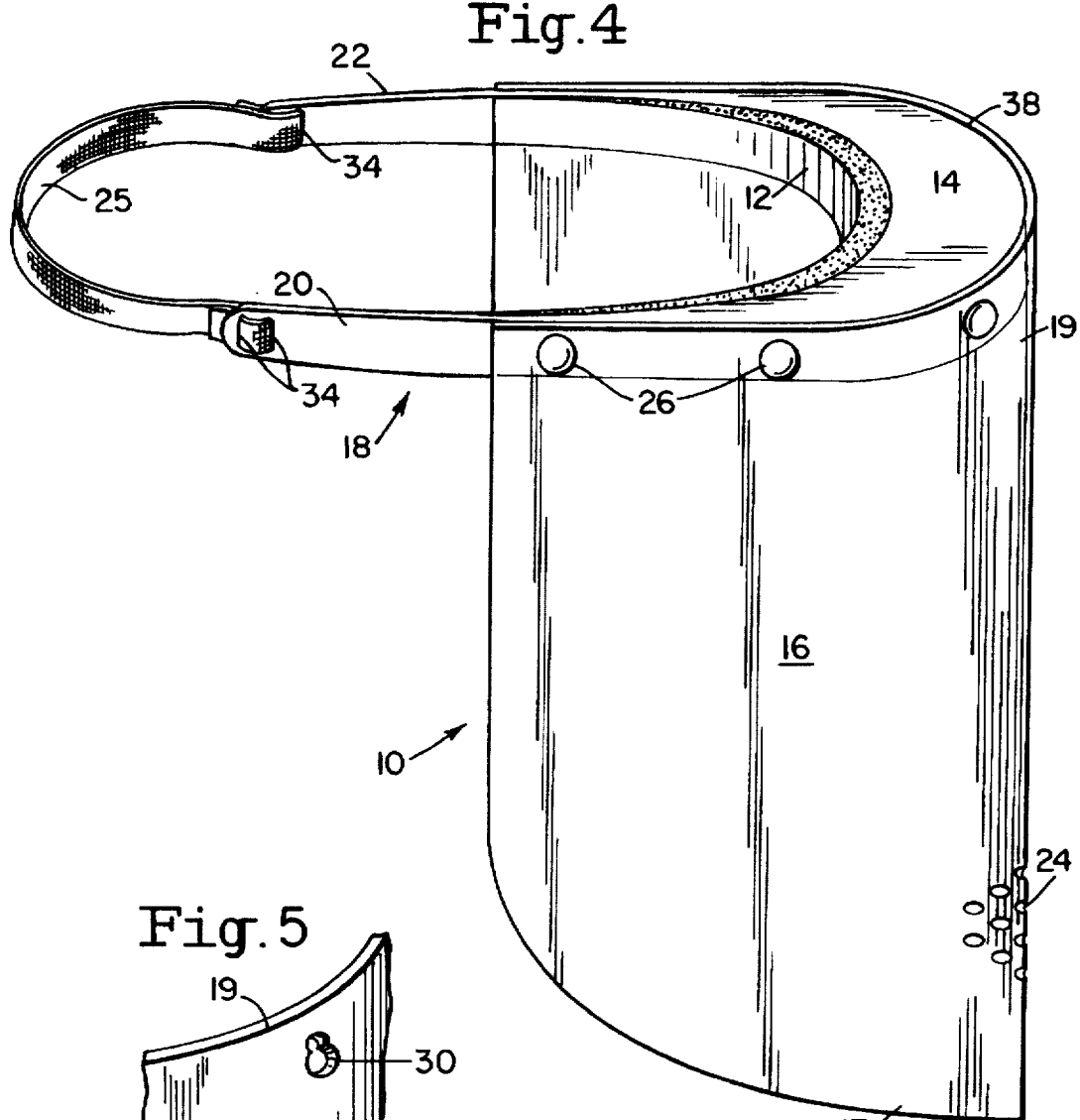
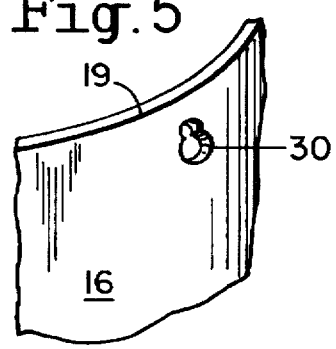
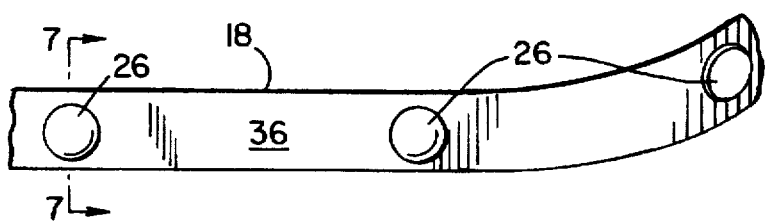

FACE SHIELD

BACKGROUND OF THE INVENTION

The present invention relates to a shield to protect the face of a wearer particularly from splattered or spattered liquids. More particularly the present invention relates to an improved face protecting shield that easily and comfortably shields the face of the wearer even if eye glasses are worn under the shield, is adaptable to a variety of different users, permits a clear and full view therethrough and permits use alone or in combination with a hat.

When painting or applying similar liquid coating material to a surface by rolling, brushing, spraying or the like, it is all too common to have the liquid material spatter and come into contact with the applicator's face. This result, of course, is quite undesirable particularly given the ingredients of many of these liquids. These problems are exacerbated when the application of paint or liquid coating material takes place overhead, as opposed to directly in front of the applicator.

A similar problem is encountered during medical procedures where personnel are faced with the potential of blood or other body fluids coming into contact with the face. Such contact can be extremely dangerous due to the potential presence of deadly or otherwise harmful viruses and pathogens.

The prior art has addressed the problems set forth above in a number of different structures. For example, FIG. 1 illustrates a prior art face shield distributed by Safe-T-Face Corporation of Beverly Hills, Calif. This particular prior art face shield is disposable and includes a transparent member affixed to a cardboard framework which folds flat for shipment and expands to the configuration illustrated in FIG. 1 when worn. The shield is secured to a wearer by an elastic band only.

In use, the cardboard framework which supports the top of the transparent member away from the face creates a large gap between the forehead of the wearer and the front of the transparent member. Spattered liquid material can therefore pass through the gap and land on the wearer's face. This face shield, therefore, only affords protection from fluid and spatters that approach the face directly from the front. Spatters approaching the top of the head will readily pass through the gap and land on the wearer's face.

FIG. 2 illustrates a second known face shield that is the subject of U.S. Pat. No. 5,303,423 to Gazara et al. This patent teaches a face shield having a flexible transparent barrier member and a spacer member affixed to a top portion of the transparent member along with an apparatus to secure the transparent member-spacer member combination to the face with the spacer member in contact with the forehead. Although adequate for some applications, this face shield also presents a number of drawbacks.

To begin with, due to the limited size and depth of the scalloped spacer member, the transparent member of the shield is frequently spaced an inch or less from the user's forehead. Due to this close spacing to the wearer's face, it becomes very difficult to use this shield and comfortably accommodate a wearer that uses eye glasses or wants to use the mask in combination with a breathing apparatus, since they will almost inevitably continue to contact the transparent barrier during use. In addition, this shield is difficult to use in conjunction with a hat, since the spacer member competes with the brim of the hat for support on the user's forehead.

Likewise, the spacer member and the device on the whole gains depend entirely upon the forehead and an elastic band to entirely support the device. This structure has a tendency to draw the bottom of the face shield away from the user's face if it is in an extremely tightened state and causes the bottom to contact the user's face and creates a gap if it loosely fastened to the wearer's head. This device likewise allows all spatters that may be coming from a location above the level of the face shield to contact the front of the shield. This leads to the necessity of frequent cleaning of the shield, rather than preventing any of the spatters from contacting the shield itself. This shield is also designed as an integral unit so that, if any portion of the shield becomes damaged or unuseable, the entire device is rendered useless.

It is therefore apparent that there exists a need in the art for an improved face shield that overcomes these drawbacks.

SUMMARY OF THE INVENTION

It is therefore an object of the present invention to provide an improved face shield that is simple and more comfortable to wear than existing shields.

It is another object of the present invention to provide a face shield that has enough space between the shield and the wearer's face to allow the wearer with glasses to utilize the shield comfortably.

It is a further object of the present invention to provide a face shield that provides the aforementioned objects in a manner that does not obscure the wearer's view.

It is yet another object of the present invention to provide a face shield that permits easy removal and replacement of a transparent face protector.

It is a still further object of the present invention to provide a face shield having an adjustable padded member that contacts the wearer's forehead.

These and other objects are provided by a face shield comprising a flexible fluid impervious transparent cover removably attached to the edge of the headband, a headband having inner and outer surfaces, first and second ends and a visor between a portion of the inner and outer surfaces that tapers from a maximum width at the midpoint between the first and second ends to a minimum at a first point spaced a distance from the first end and at a second point spaced a distance from the second end, and means for adjustably securing the shield to a wearer's head.

BRIEF DESCRIPTION OF THE DRAWINGS

The invention will be described further in connection with the attached drawings, wherein like reference numbers refer to corresponding parts throughout the several views of preferred embodiments of the invention and wherein:

FIG. 4 is a side view of one embodiment of the present invention.

FIG. 5 is a segmented front view of a preferred key hole for attachment as illustrated in FIG. 4.

FIG. 6 is an elongated front view of a portion of a preferred headband of the present invention.

FIG. 7 is a cross sectional view taken along the line 6—6 of FIG. 5.

DETAILED DESCRIPTION OF THE INVENTION

Figure 1:
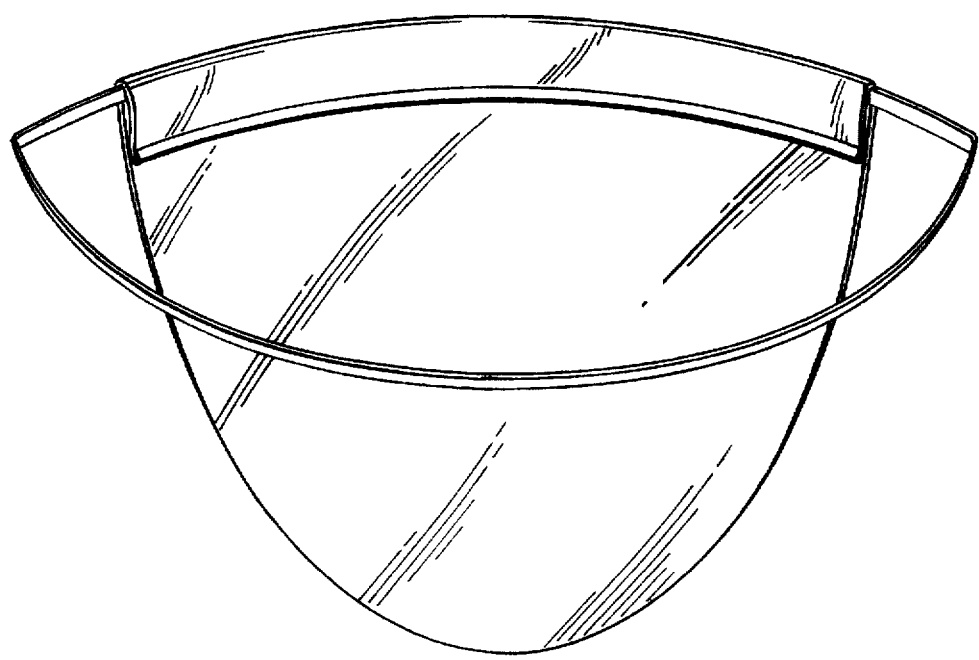
FIG. 1 is a perspective view of a prior art face shield.
Figure 2:
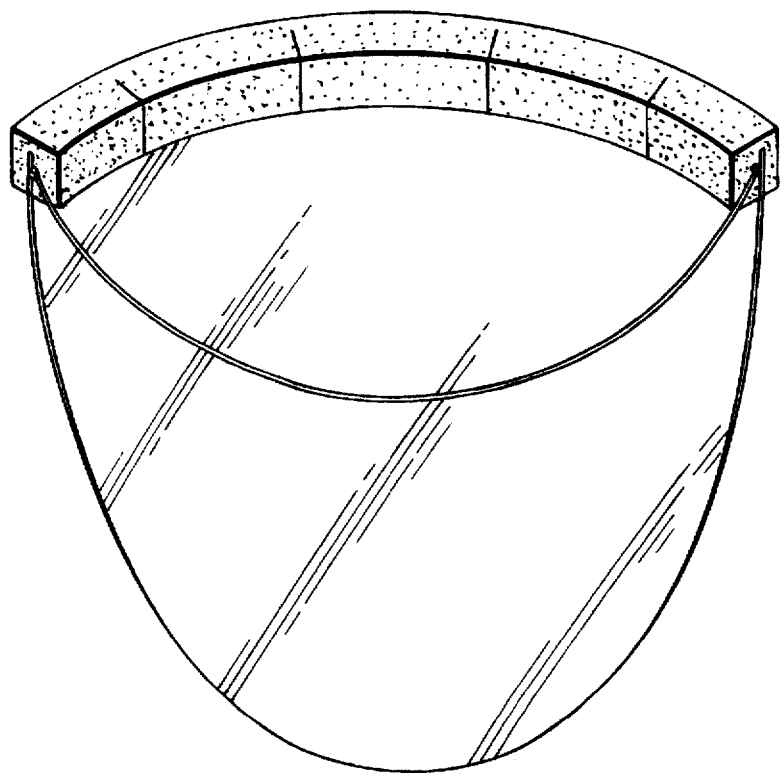
FIG. 2 is a perspective view of another prior art face shield.
Figure 3:
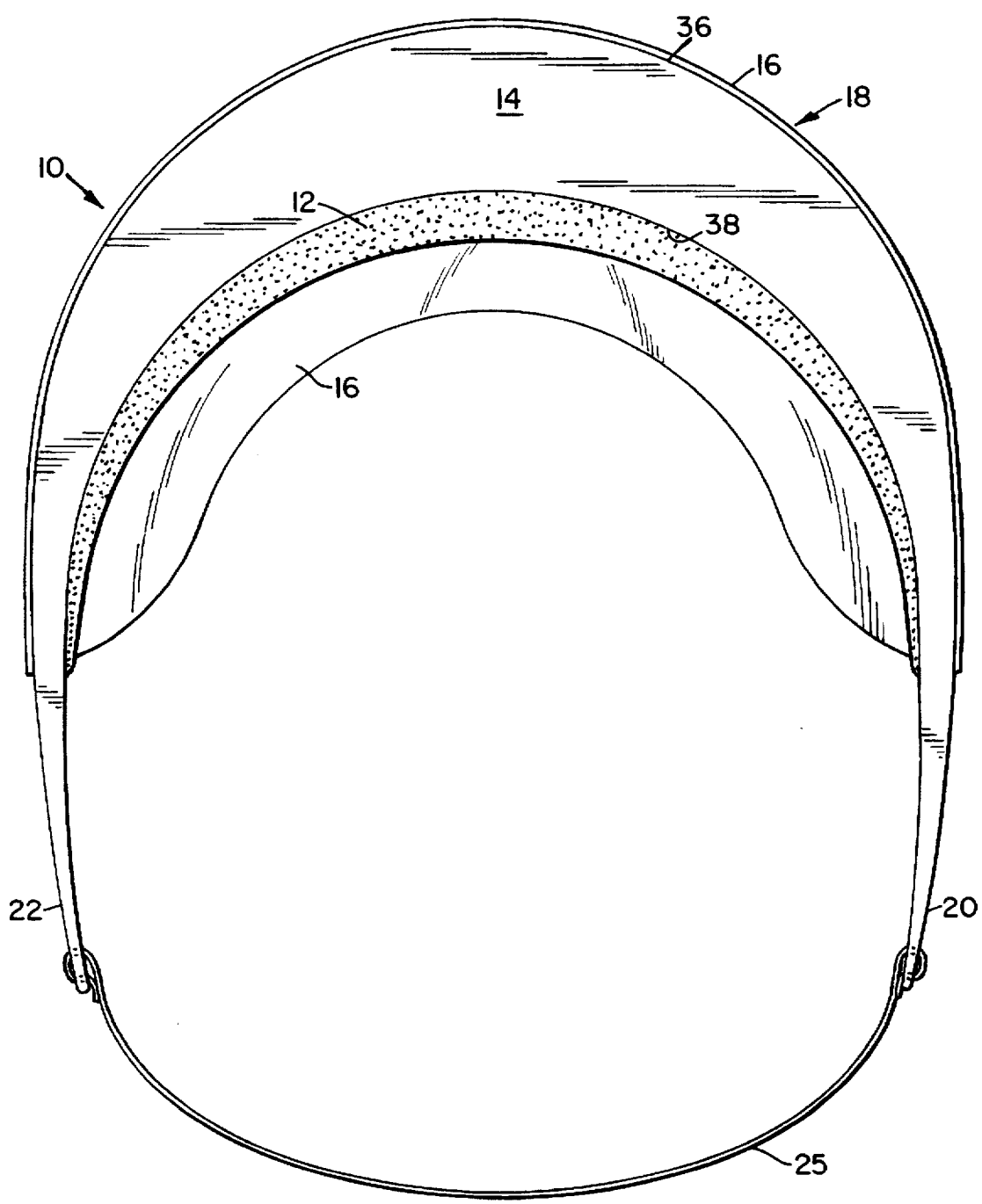
FIG. 3 is a top view of a preferred embodiment of the present invention.
Figure 9:
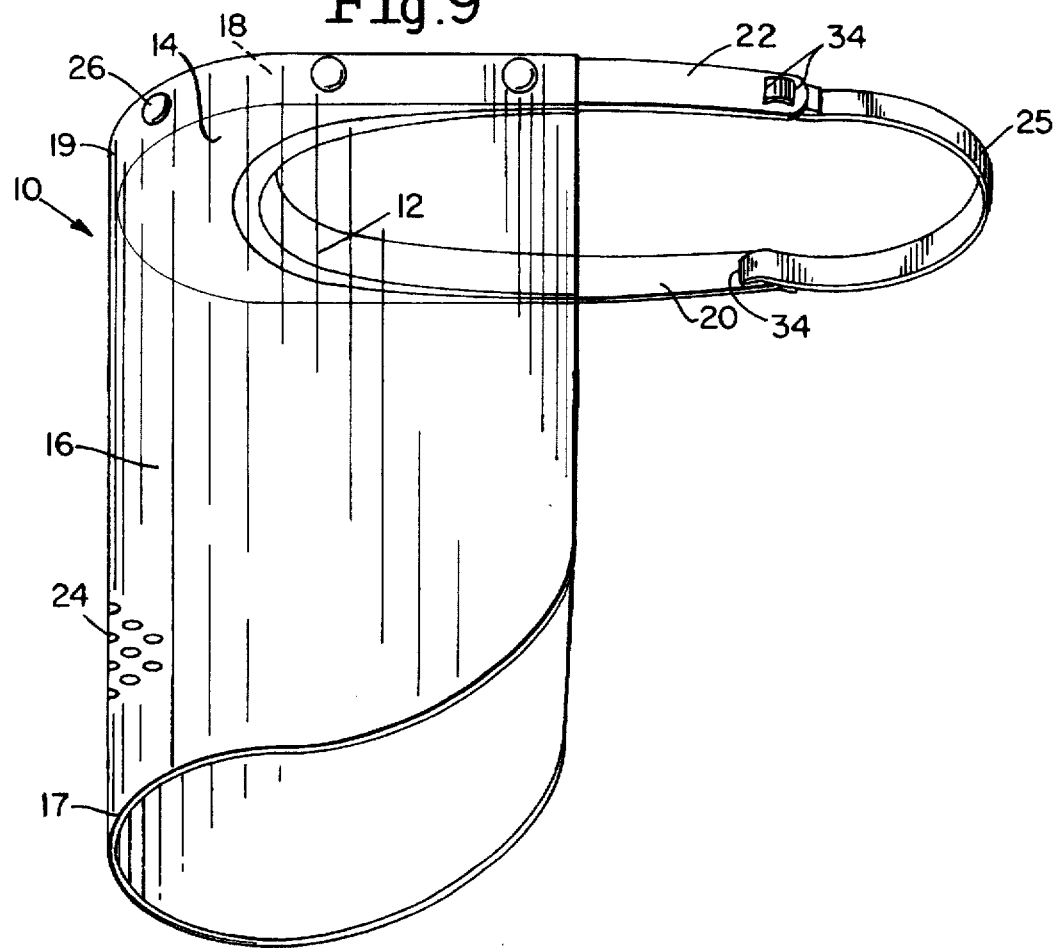
FIG. 9 is an underside perspective view of one embodiment of the present invention.

Referring now to the drawings and in particular FIGS. 3–4 and 9, a preferred embodiment of the shield 10 of the present invention will be described. It should be understood that the following description is intended to be exemplary rather than limiting and the present invention can be varied from this detailed description without departing from the scope and spirit of the claimed invention.

The shield 10 includes a flexible fluid impervious transparent face protector 16. The protector 16 is sized to cover the entire face of a wearer. The top 19 of the protector 16 is preferably flat and the bottom 17 of the protector is preferably curved.

The protector 16 is removably attached to the edge 36 of the headband 18. A variety of known attachment mechanisms including adhesive, velcro and snaps could be used to attach the protector 16. In a particularly preferred embodiment best illustrated in FIGS. 5–7 the protector 16 is provided with a plurality of keyhole slots 30 around the periphery near its top 19. The slots 30 cooperate with buttons 26 that project outwardly on stems 28 from the edge 36 of the headband 18 to removably yet tightly secure the protector 16 to the edge 36. This form of attachment is adequate to prevent any spattering through the slots 30.

Attachment is achieved by passing the larger end of the keyhole slot 30 over the button 20 then shifting the protector 16 appropriately until the stem 28 is accommodated in the narrow portion of keyhole slot 30 and the larger portion is blocked by the button 26. In this manner, if the face protector 16 becomes spattered or damaged it can easily be removed to be cleaned or replaced with another protector 16 and not require the entire shield to be disposed of.

Figure 8:
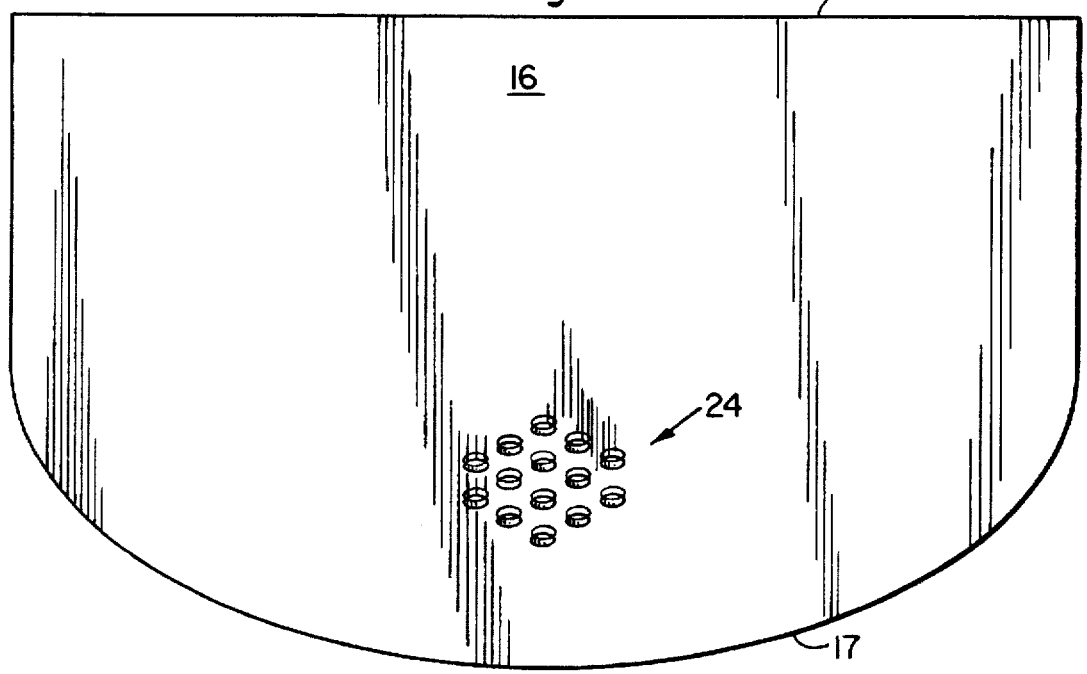
FIG. 8 is a front view of one embodiment of a face protector for use in connection with the present invention.

The protector 16 is constructed of transparent flexible plastic or similar material. It preferably includes a chemical coating to prevent glare. As illustrated in FIGS. 4 and 8 perforations 24 can be provided around the mouth area to further assist in preventing fogging of the protector 16 and increasing comfort of the wearer. These perforations 24 can be angled downwardly to further assist in preventing any liquid material from passing therethrough and contacting the wearer's face.

As described above the protector 16 is removably attached to a visor-like headband 18. The headband 18 can be formed of plastic or high impact styrene plastic molded into a visor-like form. The headband 18 features opposing semi-rigid elongated projections 20 and 22 respectively that extend along the sides of the wearer's head and assist in supporting the shield 10 by providing a slight pressure against the sides of the wearer's head. The projections are further provided with slots 34 near their ends that form a point of attachment for an elastic retainer 25 that extends between the projections and provides an adjustable attachment and supporting mechanism for the device 10 on the head of the wearer.

The headband 18 also features a visor 14 that tapers from a minimum value near the temples of the wearer to a maximum width at approximately the midpoint of the wearer's forehead when the shield 10 is in use. An inner edge 38 and the outer edge 36 are found along opposing surfaces of the visor 14. Although the maximum width of the visor 14 can vary depending upon the particular application for the present invention, widths around at least 1.5 inches have been found most preferable. In this manner, the protector 16 that is attached to the outer edge 36 of the headband 18 is spaced sufficiently away from the user's face to comfortably accommodate eye glasses and/or breathing apparatus, further assist in preventing fogging of the protector 16 and yet still provide protection from spatters. The visor 14 also provides a support to enable a user to easily wear a hat in combination with the device 10 if desired.

The headband 18 is designed to follow the contour of the wearer's head. A portion of the inner edge 38 of the headband 18 is provided with an absorbent cushioning material 12. The cushioning material 12 forms a sponge-like cushion fitted padding contoured to the shape of the headband 18. This allows a snug fit about the forehead of the user that keeps any gaps from forming between the user's forehead and the shield 10 through which spatters might otherwise travel. The absorbency of the material 12 also serves to prevent slippage of the shield due to perspiration on the wearer's forehead.

A variety of different attachment mechanisms can be used to attach the cushioning material to the inner edge 38. Preferred attachment mechanisms include permanent rigid attachment to the edge 38 using adhesives or the like. Although the material is usually of a uniform thickness, the resiliency of its cushioning material allows it to be adjusted to have a slightly differing thickness along its length if this is necessary to accommodate the forehead of the wearer.

I claim:

1. A face shield comprising:

a headband having inner and outer surfaces, first and second ends and a visor spanning an entire area between said inner and outer surfaces that tapers from a maximum width at the midpoint between said first and second ends to a minimum at a first point spaced a distance from said first end and at a second point spaced from said second end, wherein said visor is substantially rigid and aperture-free and formed of high impact styrene plastic and includes a non-sloping top surface defining a flat support between said inner and outer surfaces of said headband, said top surface is substantially perpendicular to said outer edge of said headband;

a flexible impervious transparent cover removably attached to said outer edge of said headband;

means for adjustably securing said shield to a wearer's head;

an absorbent sponge cushioning material along a portion of the inner surface of the headband to engage the forehead of the wearer;

a plurality of button projections along said outer surface of said headband and a plurality of cooperating keyhole slots along said transparent cover, each said keyhole slot having a narrow portion and an enlarged portion; and first and second slots disposed at first and second ends of said headband respectively, for receiving an elastic retainer.

2. The shield of claim 1 wherein said flexible cushioning material is attached to said inner surface of said headband whereby the width of said flexible cushioning material is variably deformable across its length.

3. The shield of claim 1 wherein said cover further comprises an anti-glare coating.

4. The shield of claim 1 wherein said cover further comprises an air vent.

5. The shield of claim 1 wherein said air vent further comprises a plurality of downwardly sloping perforations.

6. The shield of claim 2, wherein a top surface of said flexible cushioning material is flat and integral with said top surface of said visor.

* * * * *